US010468802B2

(12) United States Patent
Kobayashi et al.

(10) Patent No.: US 10,468,802 B2
(45) Date of Patent: Nov. 5, 2019

(54) TERMINAL CONNECTING STRUCTURE

(71) Applicants: Yazaki Corporation, Minato-ku, Tokyo (JP); TOYOTA JIDOSHA KABUSHIKI KAISHA, Toyota-Shi, Aichi-Ken (JP)

(72) Inventors: Hiroshi Kobayashi, Okazaki (JP); Ryutaro Yamazaki, Toyota (JP); Takayoshi Hirakawa, Kakegawa (JP); Yasuhiro Tanaka, Kakegawa (JP); Kengo Machida, Kakegawa (JP)

(73) Assignees: YAZAKI CORPORATION, Tokyo (JP); TOYOTA JIDOSHA KABUSHIKI KAISHA, Aichi-ken (JP)

( * ) Notice: Subject to any disclaimer, the term of this patent is extended or adjusted under 35 U.S.C. 154(b) by 0 days.

(21) Appl. No.: 16/011,024

(22) Filed: Jun. 18, 2018

(65) Prior Publication Data

US 2018/0366854 A1 Dec. 20, 2018

(30) Foreign Application Priority Data

Jun. 20, 2017 (JP) ................................ 2017-120072

(51) Int. Cl.
*H01R 13/11* (2006.01)
*H01R 13/187* (2006.01)
(Continued)

(52) U.S. Cl.
CPC .......... *H01R 13/111* (2013.01); *H01R 12/58* (2013.01); *H01R 13/187* (2013.01); *H01R 4/185* (2013.01)

(58) Field of Classification Search
CPC .... H01R 13/111; H01R 12/58; H01R 13/187; H01R 4/185
(Continued)

(56) References Cited

U.S. PATENT DOCUMENTS 4,550,972 A * 11/1985 Romak ................ H01R 13/111 439/839
4,720,157 A * 1/1988 Nestor ................ H01R 13/187 439/843
(Continued)

FOREIGN PATENT DOCUMENTS

CN 1511361 A 7/2004
CN 105846200 A 8/2016
(Continued)

OTHER PUBLICATIONS

Office Action dated May 14, 2019 by the Japanese Patent Office in corresponding Japanese Application No. 2017-120072.
(Continued)

*Primary Examiner* — Abdullah A Riyami
*Assistant Examiner* — Nelson R. Burgos-Guntin
(74) *Attorney, Agent, or Firm* — Sughrue Mion, PLLC

(57) ABSTRACT

A terminal connecting structure includes a male terminal having a rod-shaped portion, a female terminal having a cylindrical portion, and an elastic member provided in the cylindrical portion. The female terminal has indented portions. A projecting portion is provided on one of the rod-shaped portion and a central portion of the cylindrical portion. A cut-out portion is provided on the other of the rod-shaped portion and the central portion of the cylindrical portion. The projecting portion fits the cut-out portion when the male terminal fits in the female terminal.

4 Claims, 8 Drawing Sheets

(51) Int. Cl.
*H01R 12/58* (2011.01)
*H01R 4/18* (2006.01)

(58) Field of Classification Search
USPC .......................................... 439/846, 843, 851
See application file for complete search history.

(56) References Cited

U.S. PATENT DOCUMENTS

| | | | | |
|---|---|---|---|---|
| 5,078,622 | A * | 1/1992 | Hunt, III | H01R 13/187 439/282 |
| 6,062,919 | A * | 5/2000 | Trafton | H01R 13/187 439/843 |
| 6,656,002 | B2 * | 12/2003 | Zhao | H01R 11/22 439/787 |
| 7,115,003 | B2 * | 10/2006 | Zhao | H01R 11/22 439/851 |
| 7,387,548 | B2 * | 6/2008 | Takehara | H01R 13/187 439/843 |
| 8,079,885 | B1 * | 12/2011 | Lin | H01R 13/111 439/851 |
| 8,784,143 | B2 * | 7/2014 | Edgell | A61N 1/3752 439/246 |
| 9,905,950 | B2 * | 2/2018 | Marsh | H01R 13/113 |
| 2002/0049006 | A1 | 4/2002 | Zhao et al. | |
| 2002/0123275 | A1 | 9/2002 | Zhao et al. | |
| 2002/0187686 | A1 | 12/2002 | Zhao et al. | |
| 2004/0014370 | A1 | 1/2004 | Zhao | |
| 2005/0164566 | A1 | 7/2005 | Zhao et al. | |
| 2016/0181706 | A1 | 6/2016 | Nakano et al. | |
| 2016/0226170 | A1 | 8/2016 | Marsh et al. | |

FOREIGN PATENT DOCUMENTS

| | | | |
|---|---|---|---|
| JP | 3-64876 | A | 3/1991 |
| JP | 2009-193733 | A | 8/2009 |
| JP | 2014-123447 | A | 7/2014 |
| JP | 2016-119292 | A | 6/2016 |

OTHER PUBLICATIONS

Communication dated Jul. 3, 2019 issued by the State Intellectual Property Office of P.R. China in counterpart Chinese Application No. 201810637521.6.

* cited by examiner

TERMINAL CONNECTING STRUCTURE

CROSS-REFERENCES TO RELATED APPLICATIONS

This application is based on and claims priority from Japanese Patent Applications No. 2017-120072 filed on Jun. 20, 2017, the entire contents of which are incorporated herein by reference.

BACKGROUND

1. Field of the Invention

The invention relates to a terminal connecting structure.

2. Description of Related Art

Conventionally, there has been proposed a terminal connecting structure that includes a male terminal having a cylindrical rod-shaped portion, a female terminal having a cylindrical portion into which the rod-like portion of the male terminal is inserted, and an elastic member that is mounted in the cylindrical portion of the female terminal. The rod-shaped portion of the male terminal is held in place within the cylindrical portion of the female terminal by means of an elastic force of the elastic member. In the terminal connecting structure, the elastic member includes two ring members that are disposed along an axis and a plurality of plate springs that connect the two ring members together and that are aligned in a circumferential direction while being curved inwards. The rod-shaped portion of the male terminal is held while being biased towards an axis side of the cylindrical portion by the plurality of plate springs of the elastic member when the rod-shaped portion is inserted into the cylindrical portion of the female terminal.

In the terminal connecting structure, however, in the event that there occurs vibration whose magnitude exceeds the pressing force applied by the plurality of plate springs, the male terminal cannot be prevented from moving relative to the female terminal, and this causes contacts of the terminals to slide on each other, resulting in a risk of an increase in resistance value being called for by the wear of the contacts.

JP-A-2016-119292 proposes a terminal connecting structure in which a female terminal includes a plurality of indented portions that protrude inwards from an open side (an open side of a barrel that is provided at a rear end of the female terminal) of an inner wall of a cylindrical portion. Specifically, the plurality of indented portions include two indented portions that are provided on an open side that lies on a distal end side and two indented portions that are provided on an open side that lies on a rear end side inside the cylindrical portion. An elastic member has a plurality of plate springs that are aligned only semi-circumferentially thereon, so that a rod-shaped portion of a male terminal is biased towards the open side of the cylindrical portion where the plurality of indented portions are provided. Since the indented portions are not elastic, the indented portions can restrict the movement of the rod-shaped portion of the male terminal, thereby making it possible to reduce fears that an increase in resistance value is called for by contacts of the terminals that slide on each other.

In the terminal connecting structure described in JP-A-2016-119292, however, the plurality of indented portions work to exhibit a wedge effect to increase a contact load applied to the rod-shaped portion of the male terminal This increases an inserting force required in inserting the rod-shaped portion of the male terminal into the cylindrical portion.

On the other hand, although the inserting force can be attempted to be reduced by reducing the pressing force of the plate springs, as this occurs, it becomes difficult to restrict the movement of the rod-shaped portion of the male terminal after the male terminal fits into the female terminal.

SUMMARY

One or more embodiments relate to a terminal connecting structure that would preferably restrict a movement of a rod-shaped portion of a male terminal after the rod portion fits in a female terminal while reducing an inserting force during inserting the male terminal into the female terminal.

In accordance with one or more embodiments, a terminal connecting structure includes a male terminal having a rod-shaped portion, a female terminal having a cylindrical portion into which the rod-shaped portion is to be inserted and an elastic member provided in the cylindrical portion. The elastic member biases the rod-shaped portion towards one side of the cylindrical portion when the rod-shaped portion is inserted in the cylindrical portion. When seen from a front of the female terminal, the female terminal has a plurality of indented portions that protrude inwards from respective inner walls of areas of said one side of the cylindrical portion. The areas are positioned on both sides of a central portion of the one side of the cylindrical portion. One of a portion of the rod-shaped portion that faces the central portion of the cylindrical portion and the central portion of the cylindrical portion has a projecting portion configured to prevent the rod-shaped portion from being brought into contact with the plurality of indented portions during inserting the rod-shaped portion into the cylindrical portion. The other of the portion of the rod-shaped portion that faces the the central portion of the cylindrical portion and the central portion of the cylindrical portion has a cut-out portion into which the projecting portion fits in a state that results after the male terminal fits in the female terminal with the rod-shaped portion inserted in the cylindrical portion to allow the rod-shaped portion to be brought into contact with the plurality of indented portions.

Other aspects and advantages of the invention will be apparent from the following description and the appended claims.

BRIEF DESCRIPTION OF THE DRAWINGS

FIGS. 3A and 3B show side views of a male terminal shown in FIG. 1, in which FIG. 3A is a side view of a distal end side of the male terminal, and FIG. 3B is a partially enlarged view of FIG. 3A.

FIGS. 8A and 8B show sectional views showing a state (a fitted state) resulting after the male terminal is inserted in the cylindrical portion, in which FIG. 8A is a side sectional view showing distal end sides of both the male terminal and the female terminal, and FIG. 8B is a partially enlarged side sectional view of FIG. 8A.

DETAILED DESCRIPTION

Embodiments will be described by reference to drawings. It should be noted that the invention is not limited to embodiments that will be described below, and hence, the embodiments can be modified or altered as required without departing from the spirit and scope of the invention. In the following embodiments, although configurations thereof are partially omitted from illustration and description, in relation to the details of an omitted technique or techniques, needless to say, publically known or well-known techniques are applied to the omitted technique or techniques within a scope where no contraction to the following description is generated.

Figure 1:
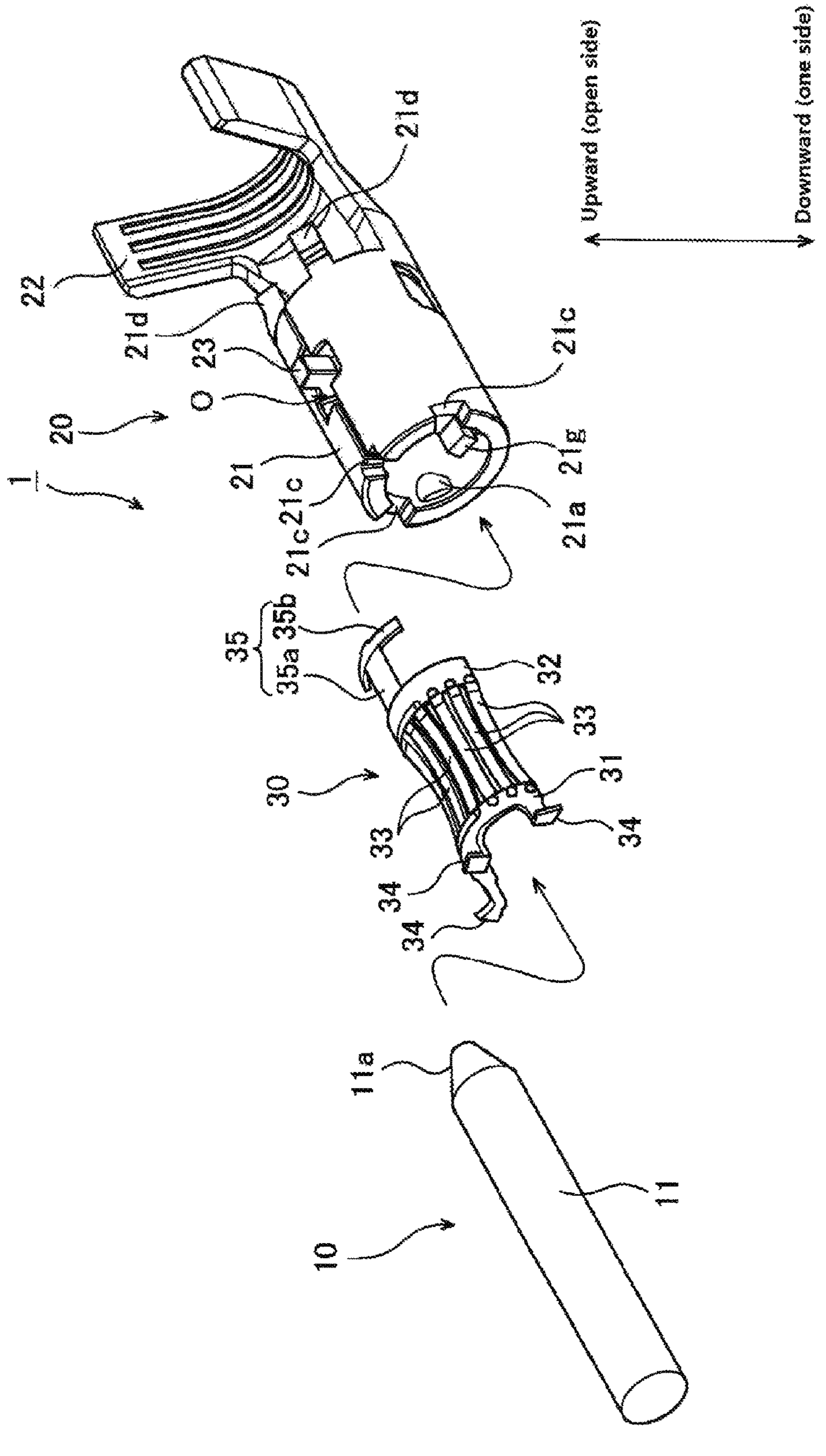
FIG. 1 is a perspective view showing a terminal connecting structure according to a first embodiment.

FIG. 1 is a perspective view showing a terminal connecting structure according to a first embodiment. As FIG. 1 shows, a terminal connecting structure according to the first embodiment includes a male terminal 10, a female terminal 20 and an elastic member 30.

The male terminal 10 is formed of a conductive metallic material and is a so-called round pin type terminal. This male terminal 10 has a cylindrical rod-shaped portion 11 and a barrel portion (not shown) that is provided consecutively to the rod-shaped portion 11 to be crimped to hold a conductive portion such as an electric wire. The male terminal 10 may include a bolt tightening portion in place of the barrel portion.

An outside diameter of the rod-shaped portion 11 is smaller than a bore diameter of a cylindrical portion (denoted by reference numeral 21, which will be described later) of the female terminal 20, so that the rod-shaped portion 11 is inserted into this cylindrical portion. A distal end 11*a* of the rod-shaped portion 11 is tapered so as to be inserted into the cylindrical portion smoothly. In this embodiment, the male terminal 10 (at least the rod-shaped portion 1) is plated.

The female terminal 20 is formed of a conductive metallic material and has a circularly cylindrical portion 21 into which the rod-shaped portion 11 of the male terminal 10 is inserted and a barrel portion 22 that is provided consecutively to the cylindrical portion 21 to be crimped to hold a conductive portion such as an electric wire. Similar to the male terminal 10, the female terminal 20 may include a bolt tightening portion in place of the barrel portion 22.

Here, since the female terminal 20 is punched out of a metallic plate and is then bent into a designed shape, an opening portion O is formed in an upper end portion (an open side of the barrel portion 22) of the cylindrical portion 21 so as to extend in a longitudinal direction of the cylindrical portion 21. Additionally, a stabilizer 23 is formed at the upper end portion of the cylindrical portion 21 to prevent an erroneous insertion of the female terminal 20 into a connector in which the female terminal 20 is to be accommodated in relation to a rotational direction.

The elastic member 30 is a member that is formed of a conductive or nonconductive metallic or resin material to be mounted in the cylindrical portion 21 of the female terminal 20. This elastic member 30 is mounted in an upper portion within the cylindrical portion 21. When the rod-shaped portion 11 of the male terminal 10 is inserted in the cylindrical portion 21 of the female terminal 20, the elastic member 30 biases the rod-shaped portion 11 downwards (towards one side) by means of an elastic force thereof to hold the rod-shaped portion in place within the cylindrical portion 21.

Figure 2:
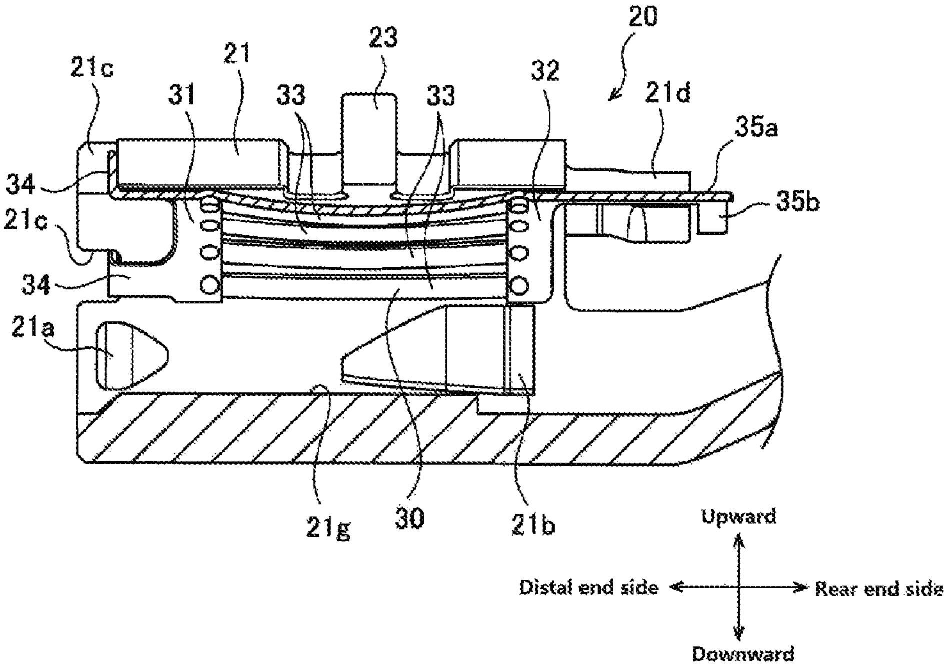
FIG. 2 is a sectional view resulting when an elastic member shown in FIG. 1 is mounted in a cylindrical portion.
Figure 3A:
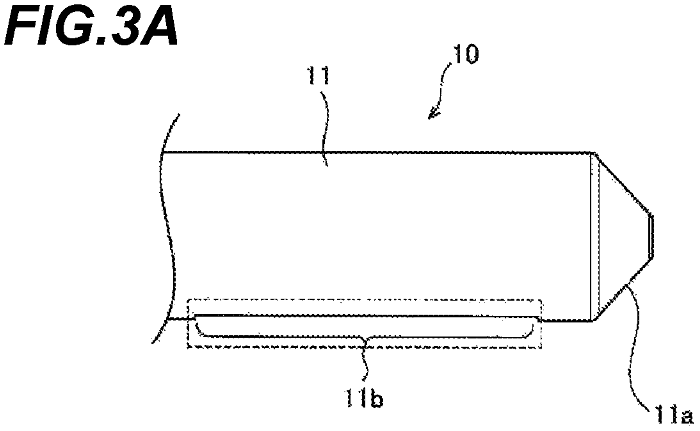
Figure 3B:
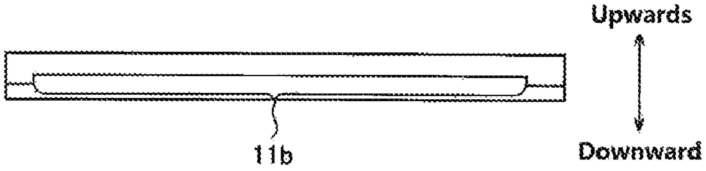
Figure 4:
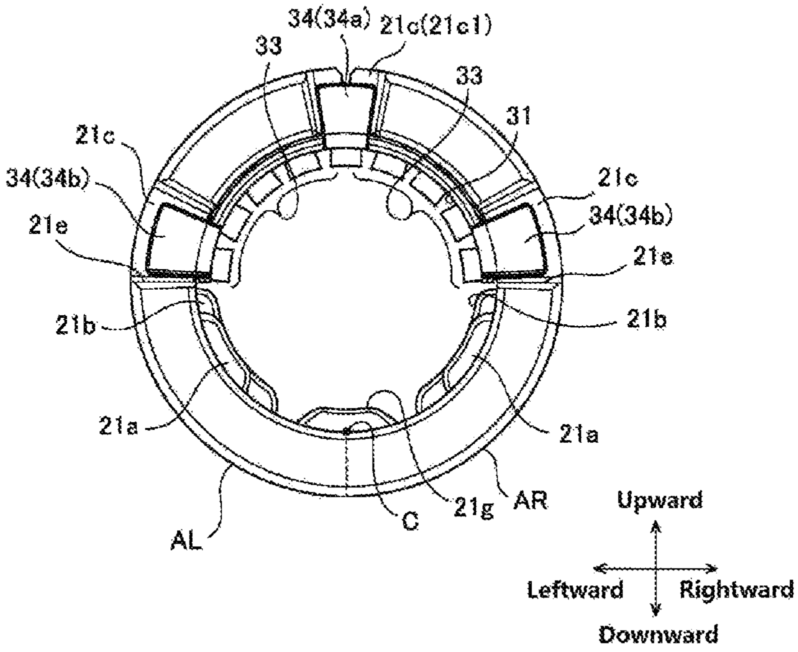
FIG. 4 is a front view resulting when the elastic member shown in FIG. 1 is mounted in the cylindrical portion.
Figure 5:
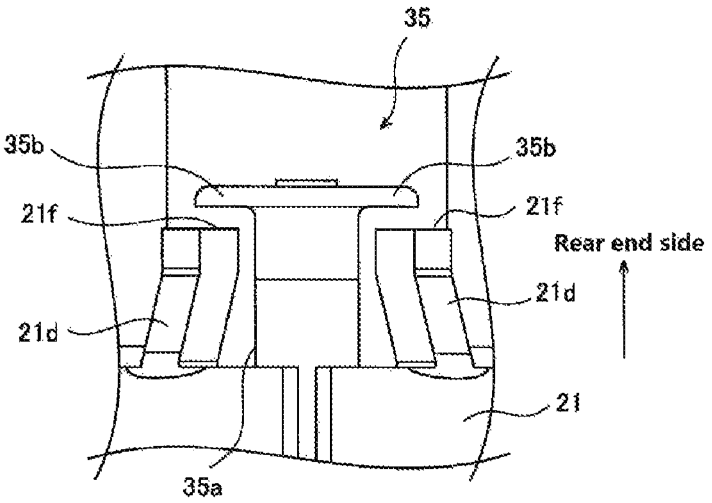
FIG. 5 is a top plan view showing a rear end side of the elastic member shown in FIG. 1 when the elastic member is mounted in the cylindrical portion of a female terminal.

Hereinafter, referring to FIGS. 1 to 5, the constituent elements will be described in detail. FIG. 2 is a sectional view resulting when the elastic member 30 shown in FIG. 1 is mounted in the cylindrical portion 21. FIGS. 3A and 3B show side views of the male terminal 10 shown in FIG. 1, in which FIG. 3A is a side view of a distal end side of the male terminal 10, and FIG. 3B is a partially enlarged view of FIG. 3A. FIG. 4 is a front view resulting when the elastic member 30 shown in FIG. 1 is mounted in the cylindrical portion 21. FIG. 5 is a top plan view showing a rear end side of the elastic member 30 shown in FIG. 1 when the elastic member 30 is mounted in the cylindrical portion 21 of the female terminal 20.

As FIGS. 1, 2 and 4 show, the female terminal 20 includes a plurality of indented portions 21*a*, 21*b* that project inwards from an inner wall of the cylindrical portion 21. The plurality of indented portions 21*a*, 21*b* are formed, for example, by hammering and include distal end side indented portions 21*a* that are formed at a lower portion of a distal end side of the female terminal 20 and rear end side indented portions 21*b* that are formed at a lower portion of a rear end side of the female terminal 20.

The distal end side indented portions 21*a* are formed individually in areas that hold therebetween a lower central portion C that lies down in a biasing direction of the elastic member 30. Namely, as the distal end side indented portions 21*a*, in total, two indented portions are provided individually in a right-hand side area AR and a left-hand side area AL that hold therebetween the central portion C; one indented portion is provided in the right-hand side area AR, and one indented portion is provided in the left-hand side area AL, when seen from the front. Similarly, as the rear end side indented portions 21*b*, in total, two indented portions are provided; one indented portion is provided in the right-hand side area AR and one indented portion is provided in the left-hand side area AL, when seen from the front. The rear end side indented portions 21*b* are formed circumferentially wider than the distal end side indented portions 21*a*.

The elastic member 30 includes two semi-ring-shaped frame members 31, 32 that are disposed along an axial of the female terminal 20 and a plurality of plate springs 33. The two semi-ring-shaped frame members 31, 32 are disposed spaced away from each other at the distal end side and the rear end side of the female terminal 20. The two semi-ring-shaped frame members 31, 32 are made up of a first frame member at the front end side (a front end side frame member) 31 and a second frame member at the rear end side (a rear end side frame member) 32. The plurality of plate springs 33 are spring members that are curved inwards (protuberant inwards) of the cylindrical portion 21 and are aligned side by side semi-circumferentially so as to connect the two frame members 31, 32 together.

In the case where the rod-shaped portion 11 of the male terminal 10 is inserted in the cylindrical portion 21, the plurality of plate springs 33 of the elastic member 30 press the rod-shaped portion 11 towards the plurality of indented portions 21*a*, 21*b*. This enables the terminal connecting structure 1 according to this embodiment to realize a strong holding force by making use of a wedge effect. As FIGS. 2 and 4 show, in this embodiment, the plurality of indented portions 21*a*, 21*b* have a curved surface structure in which a distal end protrudes outwards of the cylindrical portion 21.

Further, in this embodiment, the female terminal 20 includes a projecting portion 21*g* that projects inwards from the inner wall of the cylindrical portion 21. The projecting portion 21*g* prevents the rod-shaped portion 11 from being brought into contact with the plurality of indented portions 21*a*, 21*b* in an inserting process of the rod-shaped portion 11 and hence has a height that is sufficient to prevent the contact of the rod-shaped portion 11 with the plurality of indented portions 21*a*, 21*b*.

As FIG. 4 shows, the projecting portion 21*g* is formed on the lower central portion C. Here, when the rod-shaped portion 11 is inserted into the cylindrical portion 21, the rod-shaped portion 11 is biased downwards. To describe this more specifically, a resultant of respective forces of the plurality of plate springs 33 is directed towards the lower central portion C. The projecting portion 21*g* is provided at a location to which the resultant force of the plurality of plate springs 33 is directed. As FIG. 2 shows, the projecting portion 21*g* is formed as an elongated projection that extends slightly shorter than an axial length of the cylindrical portion 21 (an example of a length that is equal to or longer than a half the axial length of the cylindrical portion 21).

As FIG. 3 shows, a cut-out portion 11*b* is formed on the rod-shaped portion 11 of the male terminal 10 at a portion that faces the lower central portion C (that is, a lower end of the rod-shaped portion 11) when the rod-shaped portion 11 is inserted in the cylindrical portion 21. This cut-out portion 11*b* is formed in such a way as to cut the lower end of the circularly cylindrical rod-shaped portion 11 and has a length and a width that are long and wide enough for the projecting portion 21*g* to fit therein in a fitted state resulting after the cylindrical rod-shaped portion 11 is completely inserted in the cylindrical portion 21.

Further, referring to FIGS. 1 to 5, the female terminal 20 and the elastic member 30 will be described in detail.

The female terminal 20 has a plurality of (three) grooves 21*c* formed in an upper area of a front end face of the cylindrical portion 21 (refer to FIGS. 1, 2 and 4). The plurality of grooves 21*c* are each tapered in such a way as to expand in width as they extend radially outwards of the cylindrical portion 21. Further, the female terminal 20 includes pillar members 21*d* that extend further towards the rear end side thereof from a rear end face of the cylindrical portion 21 (refer to FIGS. 1, 2 and 5). As the pillar members 21*d*, two pillar members are provided laterally symmetrical with each other on an upper area of the cylindrical portion 21. The pillar members 21*d* are each shaped so as to be slightly bent inwards of the cylindrical portion 21.

As FIGS. 1, 2 and 4 show, the elastic member 30 includes a plurality of (three) tongue pieces 34 that project forwards from the first frame member 31. The three tongue pieces 34 are formed in positions that coincide with the three grooves 21*c* in a circumferential direction. Respective distal end sides of the tongue pieces 34 are bent at right angles (radially outwards of the cylindrical portion 21) to fit in the corresponding groove portions 21*c*. Due to this configuration, even though a force attempting to move the elastic member 30 towards the rear end side of the female terminal 20 is exerted on the elastic member 30, the tongue pieces 34 that fit in the corresponding grooves 21*c* comes to function to bear the force, so that the elastic member 30 is prevented from being dislocated from the cylindrical portion 21 towards the rear end side of the female terminal 20.

In particular, the distal end sides of the tongue pieces 34 are formed into the same shape as the tapered shape of the grooves 21*c* (refer to FIG. 4). Namely, the distal end sides of the three tongue pieces 34 are shaped to gradually expand in a width direction, and in the case where the distal end sides are bent at right angles, the distal end sides are shaped to expand in the width direction as they extend radially outwards of the cylindrical portion 21. In particular, in the three tongue pieces 34, a first tongue piece 34*a* that is located in an uppermost position also coincides substantially in dimension with, in the three grooves 21*c*, a corresponding groove 21*c*1 in which the first tongue piece 34*a* is to fit, whereby the elastic member 30 is prevented from being dislocated downwards. Further, the remaining two tongue pieces 34*b* are substantially located in a position lying before a three o'clock position and a position lying after a nine o'clock position, respectively, when seen from the front (in a state shown in FIG. 4). Thus, even though the elastic member 30 is caused to be dislocated downwards, the two tongue pieces 34*b* are brought into contact with side surfaces 21*e* of the corresponding grooves 21*c*, whereby the elastic member 30 is prevented from being dislocated downwards.

Further, as FIGS. 1, 2 and 5 show, the elastic member 30 includes a substantially T-shaped cantilever member 35 that extends towards the rear end side from the second frame member 32. The The cantilever member 35 includes a support member 35*a* that extends in a straight line towards the rear end side from a circumferential center of the second frame member 32 and side members 35*b* that extend to both sides from the support member 35*a*. The side members 35*b* are curved inwards at circumferentially distal end sides thereof so as to match an inner wall configuration of the cylindrical portion 21. This allows the side members 35*b* to follow the inner wall configuration of the cylindrical portion 21 when the elastic member 30 is mounted inside the cylindrical portion 21 (when the elastic member 30 is inserted into the cylindrical portion 21). Thus, bending the circumferentially distal end sides of the side members 35*b* in the way described above contributes to a smooth mounting of the elastic member 30 in the cylindrical portion 21.

Additionally, when the elastic member 30 is mounted in the cylindrical portion 21, the side members 35*b* of the cantilever member 35 approaches distal ends 21*f* of the two pillar members 21*d* (or may come into contact therewith). Due to this, even though a force attempting to move the elastic member 30 towards the rear end side of the female terminal 20 is exerted on the elastic member 30, the side members 35*b* come into contact with the distal ends 21*f* of the two pillar members 21*d*, thereby preventing the elastic member 30 from being dislocated from the cylindrical portion 21 to the distal end side of the female terminal 20.

Further, as FIGS. 2 and 4 show, the rear end side indented portions 21*b* are formed circumferentially wider than the distal end side indented portions 21*a*, so that a lower end (one side) of the second frame member 32 approaches the rear end side indented portions 21*b* in such a state that the elastic member 30 is mounted in the cylindrical portion 21. Due to this, even though the elastic member 30 is caused to be dislocated downwards, the rear end side indented portions 21*b* support the second frame member 32, thereby preventing the elastic member 30 from being dislocated downwards.

Figure 6:
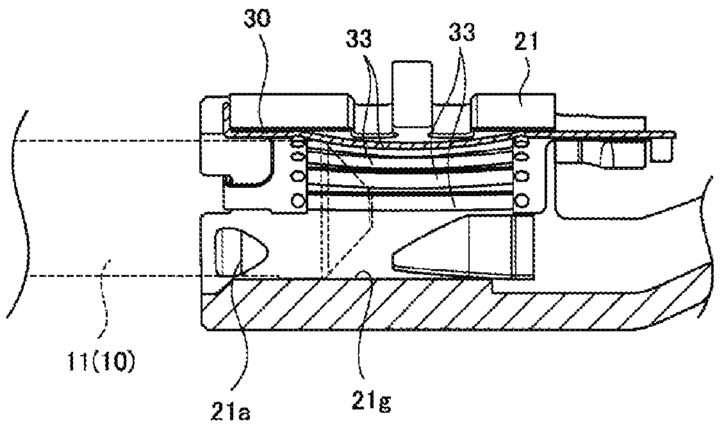
FIG. 6 is a sectional view showing an inserting process (a point in time in the middle of insertion) of the male terminal into the cylindrical portion.
Figure 7:
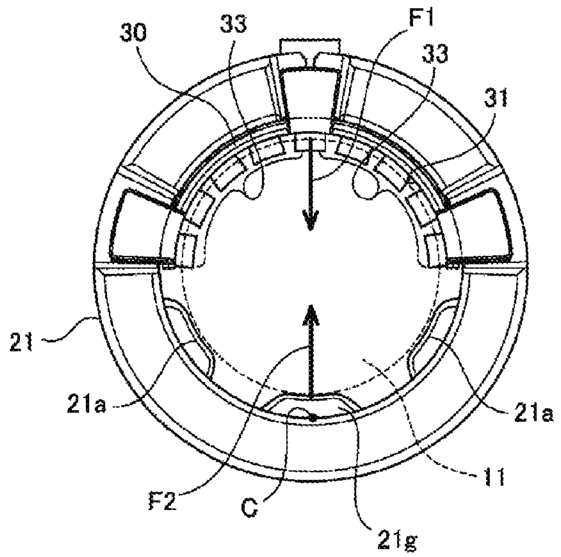
FIG. 7 is a conceptual diagram showing the inserting process (the point in time in the middle of insertion) of the male terminal into the cylindrical portion.

Next, how the terminals are connected together by the terminal connecting structure 1 according to this embodiment will be described. FIG. 6 is a sectional view showing an inserting process (a point in time in the middle of insertion) of the male terminal 10 into the cylindrical portion 21 conceptual diagram. FIG. 7 is a conceptual diagram showing the inserting process (the point in time in the middle of insertion) of the male terminal 10 into the cylindrical portion 21.

Firstly, as FIG. 6 shows, let's assume that the elastic member 30 is mounted in the upper portion of the tubular portion 21 of the female terminal 20. In this state, the rod-shaped portion 11 of the male terminal 10 is inserted into the tubular portion 21 of the female terminal 20. The female terminal 20 in which the elastic member 30 is mounted is accommodated in a terminal accommodation compartment of the connector. Additionally, the male terminal 10 is also accommodated in a terminal accommodation compartment of a mating connector. Due to this, when when the connectors are fitted together, the rod shaped portion 11 of the male connector 10 is inserted into the cylindrical portion 21 of the female terminal 20.

When the male terminal 10 and the female terminal 20 are fitted together with the rod-shaped portion 11 inserted into the cylindrical portion 21, firstly, the rod-shaped portion 11 comes into contact with the projecting portion 21*g*. As this occurs, the rod-shaped portion 11 is spaced apart from the two distal end side indented portions 21*a* while riding on the projecting portion 21*g* as shown in FIG. 7. The rod-shaped portion 11 is biased downwards by the plurality of plate springs 33 of the elastic member 30. A biasing force applied by the plurality of plate springs 33 then (a resultant force of the plurality of plate springs 33) is denoted by F1.

A force F2, which acts opposite to the resultant force F1, is generated due to the fact that the projecting portion 21*g* is provided at the lower central portion C that lies square to the resultant force F1 of the plurality of plate springs 33 and that the rod-shaped portion 11 rides on the projecting portion 21*g*. Thus, an inserting force of the rod-shaped portion 11 riding on the projecting portion 21*g* becomes F1+F2.

Figure 8A:
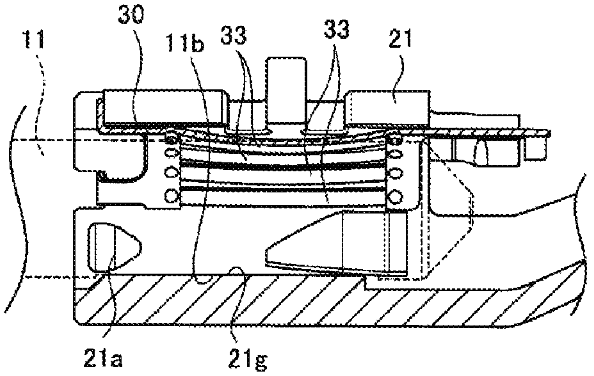
Figure 8B:
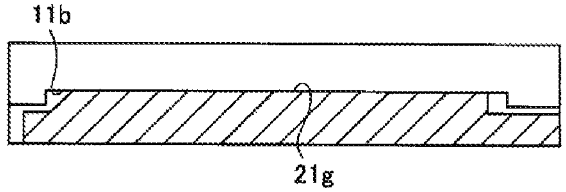
Figure 9:
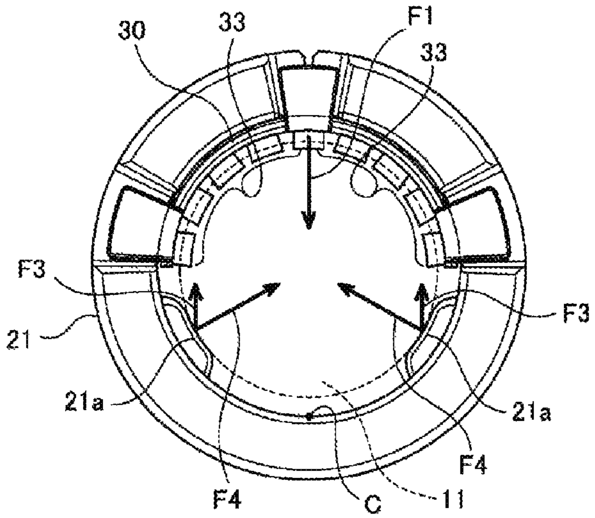
FIG. 9 is a conceptual diagram showing a state (a fitted state) after the male terminal is inserted in the cylindrical portion.

Thereafter, the rod-shaped portion 11 is inserted further, resulting in a fitted state. FIGS. 8A and 8B show sectional views showing a state resulting after the male terminal 10 is inserted in the cylindrical portion 21 (a fitted state), in which FIG. 8A is a side sectional view of a distal end side of the male terminal 10 and the distal end side of the female terminal 20, and FIG. 8B is a partially enlarged side sectional view of FIG. 8A. FIG. 9 is a conceptual diagram showing the state resulting after the male terminal 10 is inserted in the cylindrical portion 21 (the fitted state).

As FIGS. 8A and 8B show, when the rod-shaped portion 11 is inserted further, resulting in the fitted state, the projecting portion 21*g* comes to fit in the cut-out portion 11*b* of the rod-shaped portion 11. This causes the rod-shaped portion 11 to come into contact with the plurality of indented portions 21*a*, 21*b*, whereby a strong and rigid hold is realized by a wedge effect.

To describe this specifically, as FIG. 9 shows, the rod-shaped portion 11 is biased downwards with the force F1 by the plurality of plate springs 33 of the elastic member 30. On the other hand, the two distal end side indented portions 21*a* are provided in positions that do not lie square to the force F1, and forces F3, which act opposite to the force F1, are generated by the two distal end side indented portions 21*a*. Additionally, forces acting towards a center of the cylindrical portion 21 (perpendicular resisting forces), which correspond to the forces F3, are denoted by F4. Thus, a holding force of the rod-shaped portion 11 becomes F1+F4+F4. Consequently, a strong and rigid hold of the rod-shaped portion 11 is realized.

Although the rod-shaped portion 11 is described as being held by the distal end side indented portions 21*a* in FIG. 9, the female terminal 20 according to this embodiment also has the rear end side indented portions 21*b* in the cylindrical portion 21. Thus, the rod-shaped portion 11 comes into contact with not only the distal end side indented portions 21*a* but also the rear end side indented portions 21*b* in the fitted state. Thus, a strong and rigid hold like the one shown in FIG. 9 is realized by the distal end side indented portions 21*a* and the rear end side indented portions 21*b*.

In this way, with the terminal connecting structure 1 according to the first embodiment, since the projecting portion 21*g* is formed to prevent the rod-shaped portion 11 from coming into contact with the indented portions 21*a*, 21*b* in the inserting process of the male terminal 10, the rod-shaped portion 11 does not come into contact with the indented portions 21*a*, 21*b*, thereby preventing the inserting force from being enhanced by the indented portions 21*a*, 21*b*. Additionally, since the projecting portion 21*g* is provided at the portion that constitutes the central portion C on the one side of the inner wall of the cylindrical portion 21, the projecting portion 21*g* is made to lie square to the spring reaction force to bear it, whereby the inserting force would be reduced when compared with the inserting force enhanced by the indented portions 21*a*, 21*b*. In addition, since the cut-out portion 11*b* is formed so that the projecting portion 21*g* fits therein to cause the rod-shaped portion 11 to be brought into contact with the indented portions 21*a*, 21*b* after the male terminal 10 is fitted in the female terminal 20, the wedge effect would be exhibited as required after the fitment of the male terminal 10 in the female terminal 20 to restrict the movement of the rod-shaped portion 11 preferably. Thus, it is possible to restrict preferably the movement of the rod-shaped portion 11 after the fitment of the male terminal 10 in the female terminal 20 while realizing a reduction in inserting force when the male terminal 10 is inserted into the female terminal 20.

The projecting portion 21*g* is formed into the elongated projection that extends the length that is equal to or longer than a half the axial length of the cylindrical portion 21, whereby the rod-shaped portion 11 would be inserted with the reduced inserting force while being prevented from deflecting much in the axial direction.

The female terminal 20 has the tapered grooves 21*c* that expand in width as they extend radially outwards of the cylindrical portion 21 are formed on the front end face of the cylindrical portion 21. The elastic member 30 has the tongue pieces 34 that coincide in shape with the grooves 21*c* on the front end face, and the tongue pieces 34 are bent to fit in the corresponding grooves 21*c*. Due to this, even though a force attempting to move the elastic member 30 towards the rear end side of the female terminal 20 is exerted on the elastic member 30 when the elastic member 30 is mounted in the cylindrical portion 21, the tongue pieces 34 that fit in the grooves 21*c* function to bear the force. Further, the grooves 21*c* are tapered so as to expand in width as they extend radially outwards of the cylindrical portion 21, and the tongue pieces 34 are shaped to match the grooves 21*c*, whereby the elastic member 30 is restricted from moving downwards (towards the one side) by virtue of the cooperation of the tongue pieces 34 with the tapered grooves 21*c* even before the insertion of the male terminal 10, and the structure would be realized which makes it difficult for the elastic member 30 to be dislocated downwards (at one side) in the cylindrical portion 21 even before the insertion of the male terminal 10. Thus, the assembling property of the elastic member 30 to the female terminal 20 would be enhanced.

The female terminal 20 has the two pillar members 21*d* that extends towards the rear end side thereof from the rear end face of the cylindrical portion 21. The elastic member 30 has the cantilever member 35 that projects towards the rear end side of the female terminal 20, and the side members 35*b* of the cantilever member 35 come into contact with or approach the distal ends 21*f* of the two pillar members 21*d*. Due to this configuration, even though the force attempting to move the elastic member 30 towards the distal end side of the female terminal 20 is exerted on the elastic member 30, the side members 35*b* come into contact with the corresponding pillar members 21*d* to function to bear the force. Thus, it is possible to make it difficult for the elastic member 30 to be dislocated towards the distal end side of the female terminal 20, thereby making it possible to enhance the assembling property of the elastic member 30 to the female terminal 20.

In the elastic member 30, the second frame member 32 is in contact with or lies close to the rear end side indented portions 21*b*. Due to this, the elastic member 30 is restricted from moving downwards by the rear end side indented portions 21*b*, and the structure would be realized which makes it difficult for the elastic member 30 to be dislocated downwards in the cylindrical portion 21 even before the insertion of the male terminal 10. Thus, the assembling property of the elastic member 30 to the female terminal 20 would be enhanced.

Next, a second embodiment will be described. Although a terminal connecting structure according to the second embodiment is similar to that of the first embodiment but differs partially in configuration (the configurations of a male terminal 10 and a female terminal 20). Hereinafter, features that differ from the first embodiment will be described below.

Figure 10:
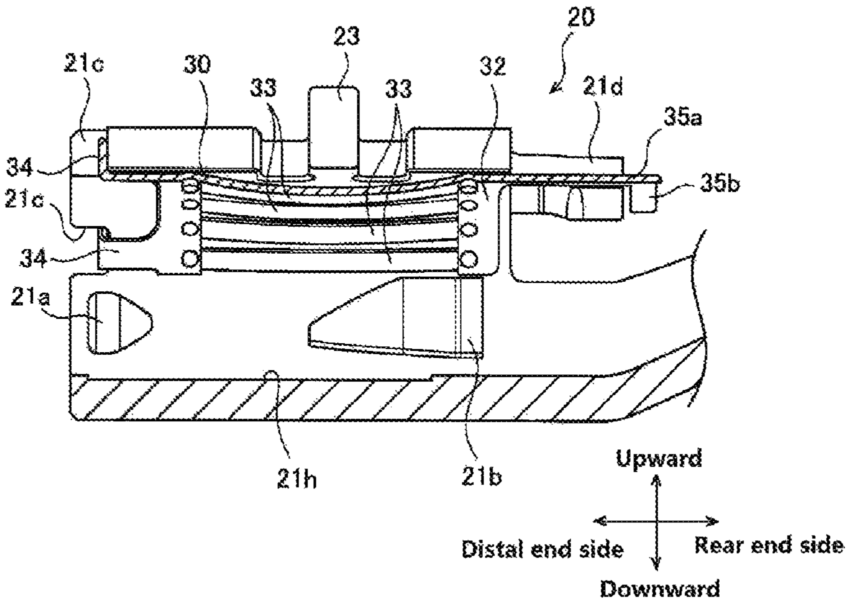
FIG. 10 is a sectional view resulting when an elastic member according to a second embodiment is inserted into a cylindrical portion.
Figure 11:
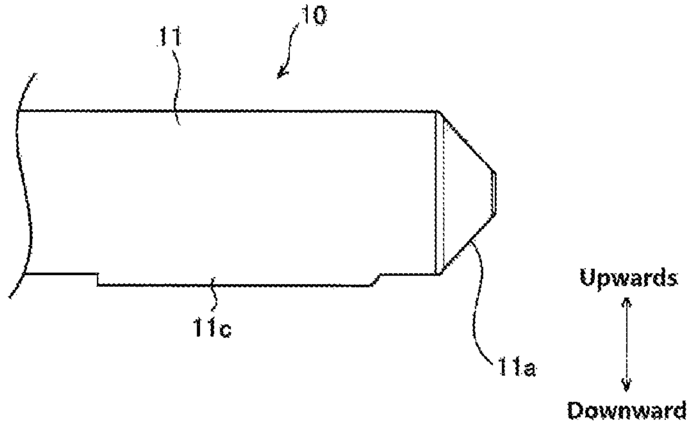
FIG. 11 is a side view of a male terminal according to the second embodiment.

FIG. 10 is a sectional view that results when an elastic member 30 according to the second embodiment is mounted in a cylindrical portion 21, and FIG. 11 is a side view of a male terminal 10 according to the second embodiment.

As FIG. 10 shows, in the second embodiment, a female terminal 20 does not include a projecting portion 21*g* but has a cut-out portion 21*h* at a central portion C. This cut-out portion 21*h* is similar to the cut-out portion formed on the male terminal 10 in the first embodiment and is formed by reducing slightly a thickness of a lower portion of a cylindrical portion 21.

As FIG. 11 shows, in the second embodiment, the male terminal 10 does not include a cut-out portion 11*b* but includes a projecting portion 11*c* at a portion facing the lower central portion C (that is, a lower end of a rod-shaped portion 11). This projecting portion 11*c* is similar to the projecting portion formed on the female terminal 20 in the first embodiment and is formed by increasing a thickness of a lower portion of the rod-shaped portion 11. The projecting portion 11*c* has a length that is equal to or longer than a half an axial length of the cylindrical portion 21 as with the first embodiment.

This projecting portion 11*c* is intended to prevent the rod-shaped portion 11 from being brought into contact with a plurality of indented portions 21*a*, 21*b* in an inserting process of the rod-shaped portion 11 and has a height that is sufficient to prevent the contact of the rod-shaped portion 11 with the plurality of indented portions 21*a*, 21*b*. The cut-out portion 21*h* has a length and a width that enable the projecting portion 11*c* to fit therein in a fitted state resulting after the rod-shaped portion 11 is inserted completely in the cylindrical portion 21.

The second embodiment configured in the way described above functions in a similar way to the first embodiment. Namely, when the rod-shaped portion 11 is inserted into the cylindrical portion 21, firstly, the projecting portion 11*c* of the rod-shaped portion 11 comes into contact with an inner wall of the cylindrical portion 21. As this occurs, the rod-shaped portion 11 is spaced apart from the two distal end side indented portions 21*a*. An inserting force of the rod-shaped portion 11 then becomes F1+F2 as with the first embodiment (refer to FIG. 7).

Thereafter, the rod-shaped portion 11 is inserted further, resulting in a fitted state. As this occurs, the projecting portion 11*c* of the rod-shaped portion 11 is allowed to fit in the cut-out portion 21*h* of the cylindrical portion 21. This causes the rod-shaped portion 11 to come into contact with the plurality of indented portions 21*a*, 21*b*, whereby a strong and rigid hold is realized by virtue of a wedge effect. A holding force of the rod-shaped portion 11 then becomes F1+F4+F4 as with the first embodiment (refer to FIG. 9).

In this way, with the terminal connecting structure 1 according to the second embodiment, the movement of the rod-shaped portion 11 would preferably be restricted after the fitment of the rod-shaped portion 11 in the cylindrical portion 21 while reducing the inserting force required when the male terminal 10 is inserted into the female terminal 20. Additionally, the substantially cylindrical rod-shaped portion 11 would be inserted with the reduced inserting force while being prevented from deflecting much in an axial direction. Further, the assembling property of the elastic member 30 to the female terminal 20 would be enhanced.

Next, a third embodiment will be described. A terminal connecting structure according to the third embodiment is similar to that of the first embodiment but differs partially in configuration (the configurations of a male terminal 10 and a female terminal 20). Hereinafter, features that differ from the first embodiment will be described.

Figure 12:
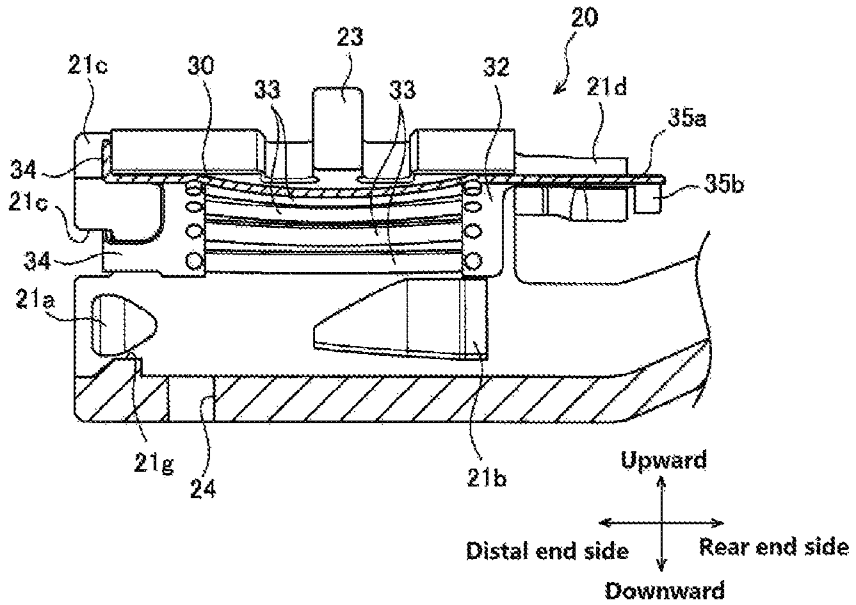
FIG. 12 is a sectional view resulting when an elastic member according to a third embodiment is mounted in a cylindrical portion.
Figure 13:
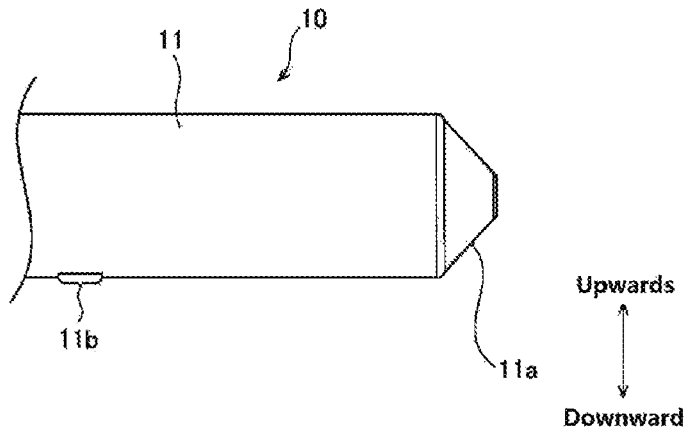
FIG. 13 is a side view of a male terminal according to the third embodiment.

FIG. 12 is a sectional view resulting when an elastic member 30 according to the third embodiment is mounted in a cylindrical portion 21. FIG. 13 is a side view of a male terminal 10 according to the third embodiment.

As FIG. 12 shows, in the third embodiment, a female terminal 20 includes a through hole 24 on a distal end side of a lower central portion C inside a cylindrical portion 21. The through hole 24 is intended for a projection to fit in it to prevent the female terminal 20 accommodated in a connector from being dislocated from the connector.

A projecting portion 21*g* in the third embodiment is intended to prevent a rod-shaped portion 11 from being brought into contact with a plurality of indented portions 21*a*, 21*b* in an inserting process of the rod-shaped portion 11 into the cylindrical portion 21, as with the projecting portion 21*g* described in the first embodiment. However, the projecting portion 21*g* of the third embodiment has a length that is shorter than that of the projecting portion 21*g* of the first embodiment. Namely, the projecting portion 21*g* of the third embodiment is provided at a portion that lies further towards a distal end side of the female terminal 20 than the through hole 24 that is formed on the distal end side of the lower central portion C, and the length of the projecting portion 21*g* is limited to such an extent that the projecting portion 21*g* does not disturb the formation of the through hole 24.

As FIG. 13 shows, in the third embodiment, the male terminal 10 includes a cut-out portion 11*b* as with the male terminal 10 of the first embodiment. This cut-out portion 11*b* has a length that matches the length of the projecting portion 21*g* and is formed to extend shorter in a longitudinal direction of the rod-shaped portion 11 than that of the first embodiment.

The third embodiment configured in the way described above also functions in a similar way to the first embodiment. In the inserting process of the rod-shaped portion 11, firstly, the projecting portion 21*g* comes into contact with the rod-shaped portion 11, whereby the rod-shaped portion 11 is prevented from coming into contact with the two distal end side indented portions 21*a,* and an inserting force of the rod-shaped portion 11 becomes F1+F2, as with the first embodiment (refer to FIG. 7).

Thereafter, when the rod-shaped portion 11 is inserted further, resulting in a fitted state, the projecting portion 21*g* fits in a cut-out portion 21*h,* causing the rod-shaped portion 11 to come into contact with the plurality of indented portions 21*a,* 21*b*. Due to this, a strong and rigid hold is realized by virtue of a wedge effect, and a holding force becomes F1+F4+F4, as with the first embodiment (refer to FIG. 9).

In this way, with the terminal connecting structure 1 according to the third embodiment, the movement of the rod-shaped portion 11 would preferably be restricted after the fitment of the rod-shaped portion 11 in the cylindrical portion 12 while reducing the inserting force required when the male terminal 10 is inserted into the female terminal 20. Additionally, the assembling property of the elastic member 30 to the female terminal 20 would be enhanced.

Further, with the third embodiment, the female terminal 20 has the projecting portion 21*g* on an inner wall of the cylindrical portion 21 and also has the through hole 24 in which the projection on the connector that accommodates therein the female connector 20 fits on a rear end side of the projecting portion 21*g*. Thus, the projecting portion 21*g* would be formed without disturbing the formation of the through hole 24 while forming the through hole 24 or the fixing location where the connector is fixed at the portion constituting the central portion C.

Next, a fourth embodiment will be described. Although a terminal connecting structure according to the fourth embodiment is similar to that of the first embodiment but differs partially in configuration (the configurations of a female terminal 20 and an elastic member 30). Hereinafter, features that differ from the first embodiment will be described.

Figure 14:
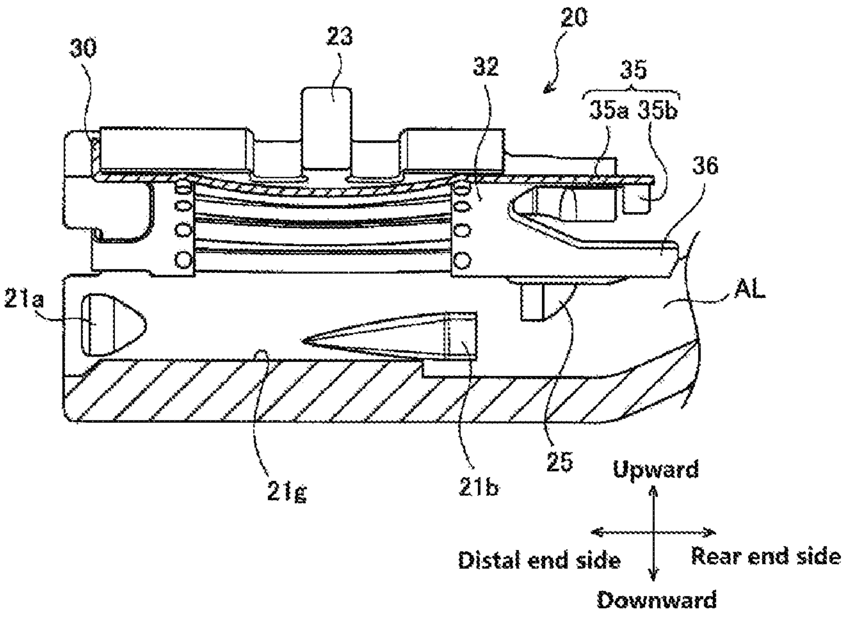
FIG. 14 is a sectional view resulting when an elastic member according to a fourth embodiment is inserted into a cylindrical portion.

FIG. 14 is a sectional view resulting when an elastic member 30 according to a fourth embodiment is mounted in a cylindrical portion 21 of a female terminal 20. As FIG. 14 shows, the elastic member 30 according to the fourth embodiment includes an extending portion 36 that extends towards a rear end side of the female terminal 20 from a second frame member 32. Although only one extending portion 36 is shown in FIG. 14, in total, two extending portions 36 are provided so that one extending portion 36 extends from each of both end portions of the second frame member 32. These two extending portions 36 extend further towards the rear end side than a cantilever member 35, and distal ends of the extending portions 36 project further towards the rear end side than side members of the cantilever member 35.

In the female terminal 20 according to the fourth embodiment, rear end side indented portions 21*b* are not wider in a circumferential direction than distal end side indented portions 21*a* but have substantially the same circumferential width as that of the distal end side indented portions 21*a*. Further, the female terminal 20 includes a projecting portion 25 at a portion thereon that lies further towards the rear end side than and slightly above the rear end side indented portions 21*b*. The projecting portion 25 projects radially inwards of the cylindrical portion 21 as with the plurality of distal end side and rear end side indented portions 21*a,* 21*b*. Although only one projecting portion 25 is shown in FIG. 14 due to only a left-hand side area AL of the female terminal 20 being shown therein, another projecting portion 25 is also provided in a right-hand side area AR. Namely, the female terminal 20 has two projecting portions 25.

Here, the elastic member 30 lies close to (or may be in contact with) the projecting portions 25 at lower ends (or sides) of the extending portions 36 thereof in such a state that the elastic member 30 is mounted in the cylindrical portion 21. Due to this, even though the elastic member 30 is caused caused to be dislocated downwards, the projecting portions 25 come to support the elastic member 30 via the extending portions 36, whereby the elastic member 30 is prevented from being dislocated downwards.

In this way, with the terminal connecting structure 1 according to the fourth embodiment, as with the first embodiment, the movement of the rod-shaped portion 11 would preferably be restricted after the fitment of the rod-shaped portion 11 in the cylindrical portion 21 while reducing the inserting force required when the male terminal 10 is inserted into the female terminal 20. Additionally, the substantially cylindrical rod-shaped portion 11 would be inserted with the reduced inserting force while being prevented from deflecting much in an axial direction. Further, the assembling property of the elastic member 30 to the female terminal 20 would be enhanced.

Further, with the fourth embodiment, the elastic member 30 has the extending portions 36 that extend towards the rear end side from the second frame member 32, and the female terminal 20 includes the projecting portions 25 that lies in contact with or close to the lower ends of the extending portions 36. Due to this configuration, the elastic member 30 is restricted from moving downwards by virtue of the cooperation of the extending portions 36 with the projecting portions 25, whereby it becomes difficult for the elastic member 30 to be dislocated downwards in the cylindrical portion 21 even before the insertion of the male terminal 10. Thus, the assembling property of the elastic member 30 to the female terminal 20 would be enhanced.

Thus, while the invention has been described heretofore based on the embodiments, the invention is not limited to those embodiments. Hence, modifications or alterations may be made to the embodiments without departing from the spirit and scope of the invention. Alternatively, the techniques described in the embodiments may be combined together as required. Further, as many techniques in the embodiments as possible may be combined with other techniques available as required.

For example, the terminal connecting structure 1 according to the embodiments include the two types of indented portions 21*a,* 21*b* that are the distal end side indented portions 21*a* and the rear end side indented portions 21*b*. However, the invention is not limited thereto, and hence, the terminal connecting structure 1 may include only either of the two types of indented portions, provided that the rod-shaped portion 11 of the male terminal 10 would be held as required. Alternatively, the terminal connecting structure 1 may include other indented portions of a third type or the like. In addition, although the female terminal 20 includes the two distal end side indented portions 21*a*, the invention is not limited thereto, and hence, the female terminal 20 may include three or more distal end side indented portions. This will be true with the rear end side indented portions 21*b*. Further, the two distal end side indented portions 21*a* are provided on the same cross section that is at right angles to the axis of the cylindrical portion 21. However, if possible, the two distal end side indented portions may be formed offset from each other in the axial direction. This will be true with the two types of the rear end side indented portions 21*b*.

In the embodiments, although the three grooves 21*c* and the tree tongue pieces 34 are provided, the invention is not limited thereto. Hence, two or less or four or more grooves 21 and tongue pieces 34 may be provided. Further, although the two pillar members 21*d* are provided, one or three or more pillar members 21*d* may be provided. In addition, the cantilever member 35 has the T-shape when seen from the top thereof, but the invention is not limited thereto. Hence, the cantilever member 35 may have other shapes including an L-shape or the like.

Additionally, in mounting the elastic member 30 in the cylindrical portion 21, the elastic member 30 may be mounted using other methods without making use of the tongue pieces 34. The portion where the elastic member 30 is provided in the cylindrical portion 21 is not limited to the upper portion in the cylindrical portion 21, and hence, the elastic member 30 may be mounted in other portions in the cylindrical portion 21 such as a lower portion therein.

In accordance with exemplary embodiments as shown in the drawings, a terminal connecting structure includes a male terminal 10 including a rod-shaped portion 11, a female terminal 20 having a cylindrical portion 21 into which the rod-shaped portion 11 is to be inserted, and an elastic member 30 provided in the cylindrical portion 21. The elastic member 30 biases the rod-shaped portion 11 towards one side of the cylindrical portion 21 when the rod-shaped portion 11 is inserted in the cylindrical portion 21. When seen from a front of the female terminal 20, the female terminal 20 has a plurality of indented portions 21*a*, 21*b* that protrude inwards from respective inner walls of areas of the one side of the cylindrical portion 21. The areas are positioned on both sides of a central portion C of the one side of the cylindrical portion 21. One of a portion of the rod-shaped portion 11 that faces the central portion C of the cylindrical portion 21 and the central portion C of the cylindrical portion 21 has a projecting portion 21*g* configured to prevent the rod-shaped portion 11 from being brought into contact with the plurality of indented portions 21*a*, 21*b* during inserting the rod-shaped portion 11 into the cylindrical portion 21. The other of the portion of the rod-shaped portion 11 that faces the central portion C of the cylindrical portion 21 and the central portion C of the cylindrical portion 21 has a cut-out portion 11*b* into which the projecting portion 21*g* fits in a state that results after the male terminal 10 fits in the female terminal 20 with the rod-shaped portion 11 inserted in the cylindrical portion 21 to allow the rod-shaped portion 11 to be brought into contact with the plurality of indented portions 21*a*, 21*b*.

According to the structure, the projecting portion is formed to prevent the rod-shaped portion from being brought into contact with the indented portions in the inserting process of the male terminal, and hence, the rod-shaped portion does not contact the indented portions, whereby the inserting force is prevented from being enhanced by the indented portions. In addition, the projecting portion is provided at the portion of the one side of the cylindrical portion that constitutes the central portion thereof, and hence, the projecting portion lies square to a direction in which the spring reaction force is applied and hence comes to bear the spring reaction force, thereby making it possible to reduce the inserting force when compared with the inserting force that is enhanced by the indented portions. In addition, the cut-out portion is formed into which the projecting portion fits after the male terminal fits in the female terminal, allowing the rod-shaped portion to be brought into contact with the indented portions. Thus, a wedge effect would be exhibited as required after the male terminal fits in the female terminal, thereby making it possible to restrict the movement of the rod-shaped portion preferably. Consequently, it is possible to restrict the movement of the rod-shaped portion preferably after the male terminal fits in the female terminal while realizing a reduction in inserting force when the male terminal is being inserted.

In the terminal connecting structure, the projecting portion 21*g* may include an elongated projection having a length that is equal to or longer than a half an axial length of the cylindrical portion 21.

According to the structure, the projecting portion constitutes the elongated projection that extends the length that is equal to or longer than a half the axial length of the cylindrical portion, and hence, the rod-shaped portion would be inserted with a reduced inserting force while being prevented from deflecting much in the axial direction.

In the structure, the female terminal 20 may include the projecting portion 21*g* at the central portion C and a through hole 24 at a rear end side of the projecting portion 21*g*, and the through hole 24 may be configured to fit with a projection on a connector that accommodates the female terminal therein.

According to the structure, the female terminal has the projecting portion on the inner wall of the cylindrical portion and the through hole at the rear end side of the projecting portion in which the projection on the connector that accommodates the female terminal therein fits. Therefore, although the fixing portion where the connector is fixed is formed at the portion that constitutes the central portion, the projecting portion would be formed without obstructing the fixing portion.

In the terminal structure, the elastic member 30 may have two frame members 31, 32 that have semi-ring-shapes and that are spaced away from each other at a distal end side and a rear end side, and a plurality of plate springs 33 that connect the two frame members 31, 32 together and that are curved inwards of the cylindrical portion 21. The plurality of indented portions 21*a*, 21*b* may have two or more indented portions that are provided at each of a distal end side and a rear end side of an interior of the cylindrical portion 21. A frame member 32 at the rear end side of the two frame members 31, 32 may be in contact with or lies close to the indented portion 21*b* at the rear end side.

According to the structure, the elastic member is in contact with or lies close to the indented portions at the rear end side at the frame member at the rear end side. Due to this, the elastic member is restricted from moving towards the one side by the indented portions at the rear end side, whereby the elastic member would be prevented from being dislocated towards the one side of the cylindrical portion even before the male terminal is inserted thereinto. Thus, the assembling property of the elastic member to the female terminal would be enhanced.

In accordance with the exemplary embodiment, the terminal connecting structure would restrict the movement of the rod-shaped portion after the rod-shaped portion fits in the female terminal while reducing an inserting force when the male terminal is inserted into the female terminal.

DESCRIPTION OF REFERENCE NUMERALS AND CHARACTERS

1: terminal connecting structure; 10: male terminal; 11: rod-shaped portion; 11*b:* cut-out portion; 11*c:* projecting portion; 20: female terminal; 21: cylindrical portion; 21*a,* 21*b:* plurality of indented portions; 21*a:* distal end side indented portion; 21*b:* rear end side indented portion; 21*c:* groove; 21*d:* pillar member; 21*f:* distal end; 21*g:* projecting portion; 21*h:* cut-out portion; 24: through hole; 25: projecting portion; 30: elastic member; 31, 32: frame member; 31: first frame member (distal end side frame member); 32: second frame member (rear end side frame member); 33: plurality of plate springs; 34: tongue piece; 35: cantilever member; 35*a:* support member; 35*b:* side member; 36: extending portion; AL: left-hand side area; AR: right-hand side area; C: central portion.

What is claimed is:

1. A terminal connecting structure comprising:

a male terminal including a rod-shaped portion;

a female terminal having a cylindrical portion into which the rod-shaped portion is to be inserted; and an elastic member provided in the cylindrical portion, wherein the elastic member biases the rod-shaped portion towards one side of the cylindrical portion when the rod-shaped portion is inserted in the cylindrical portion, wherein, when seen from a front of the female terminal, the female terminal has a plurality of indented portions that protrude inwards from respective inner walls of areas of said one side of the cylindrical portion, wherein said areas are positioned on both sides of a central portion of said one side of the cylindrical portion, wherein one of a portion of the rod-shaped portion that faces the central portion of the cylindrical portion and the central portion of the cylindrical portion has a projecting portion configured to prevent the rod-shaped portion from being brought into contact with the plurality of indented portions during inserting the rod-shaped portion into the cylindrical portion, and wherein the other of the portion of the rod-shaped portion that faces the central portion of the cylindrical portion and the central portion of the cylindrical portion has a cut-out portion into which the projecting portion fits in a state that results after the male terminal fits in the female terminal with the rod-shaped portion inserted in the cylindrical portion to allow the rod-shaped portion to be brought into contact with the plurality of indented portions.

2. The terminal connecting structure according to claim 1, wherein the projecting portion includes an elongated projection having a length that is equal to or longer than a half an axial length of the cylindrical portion.

3. The terminal connecting structure according to claim 1, wherein the female terminal includes the projecting portion at the central portion and a through hole at a rear end side of the projecting portion, and wherein the through hole is configured to fit with a projection on a connector that accommodates the female terminal therein.

4. The terminal connecting structure according to claim 1 wherein the elastic member has two frame members that have semi-ring-shapes and that are spaced away from each other at a distal end side and a rear end side, and a plurality of plate springs that connect the two frame members together and that are curved inwards of the cylindrical portion, wherein the plurality of indented portions have two or more indented portions that are provided at each of a distal end side and a rear end side of an interior of the cylindrical portion, and wherein a frame member at the rear end side of the two frame members is in contact with or lies close to the indented portion at the rear end side.

* * * * *